US012649508B2

(12) United States Patent
Kitt

(10) Patent No.: US 12,649,508 B2
(45) Date of Patent: Jun. 9, 2026

(54) VIRAL DISINFECTANT APPARATUS

(71) Applicant: Vinita Kitt, Montgomery, AL (US)

(72) Inventor: Vinita Kitt, Montgomery, AL (US)

( * ) Notice: Subject to any disclaimer, the term of this patent is extended or adjusted under 35 U.S.C. 154(b) by 396 days.

(21) Appl. No.: 17/246,881

(22) Filed: May 3, 2021

(65) Prior Publication Data

US 2022/0348245 A1      Nov. 3, 2022

(51) Int. Cl.
| *B62B 5/06* | (2006.01) |
| *A61L 2/238* | (2006.01) |
| *A61L 101/26* | (2006.01) |

(52) U.S. Cl.
CPC .............. *B62B 5/069* (2013.01); *A61L 2/238* (2013.01); *A61L 2101/26* (2020.08); *A61L 2202/16* (2013.01)

(58) Field of Classification Search
CPC ...... B62B 5/069; A61L 2/238; A61L 2101/26; A61L 2202/16
See application file for complete search history.

(56) References Cited

U.S. PATENT DOCUMENTS

| D298,077 | S | * | 10/1988 | Goodwin | ................ B62B 5/069 |
| | | | | | D34/27 |
| 5,820,142 | A | * | 10/1998 | Duer | ......................... A61L 2/22 |
| | | | | | 150/154 |
| 6,065,764 | A | * | 5/2000 | Moseley | ................... B62B 5/06 |
| | | | | | 280/33.993 |
| 6,981,707 | B1 | * | 1/2006 | Dandy | ...................... B62B 5/06 |
| | | | | | 280/33.993 |
| D605,824 | S | * | 12/2009 | DiMento | ........................ D34/27 |
| 2005/0267233 | A1 | * | 12/2005 | Joshi | ..................... E05B 1/0069 |
| | | | | | 424/618 |
| 2016/0200341 | A1 | * | 7/2016 | Hall | ........................ B62B 5/069 |
| | | | | | 280/33.992 |
| 2020/0398883 | A1 | * | 12/2020 | Sisson | ................... E05B 1/0069 |
| 2022/0054680 | A1 | * | 2/2022 | Loucks | ...................... C09J 7/38 |
| 2022/0281504 | A1 | * | 9/2022 | Van Heyningen | ........ B32B 1/08 |

FOREIGN PATENT DOCUMENTS

WO        WO-2020237003 A1 * 11/2020    ............. C08K 3/015

* cited by examiner

*Primary Examiner* — John D Walters
(74) *Attorney, Agent, or Firm* — Ronald D. Baker, Esq.

(57)        ABSTRACT

The present invention is a viral disinfectant apparatus for conveniently providing a method of preventing viruses from coming in contact with a user's hands. In particular, the invention allows a user to conveniently install and remove the apparatus to a shopping cart while in public spaces. The proposed embodiment provides a unique experience for a user by providing a safe experience for the general public.

2 Claims, 6 Drawing Sheets

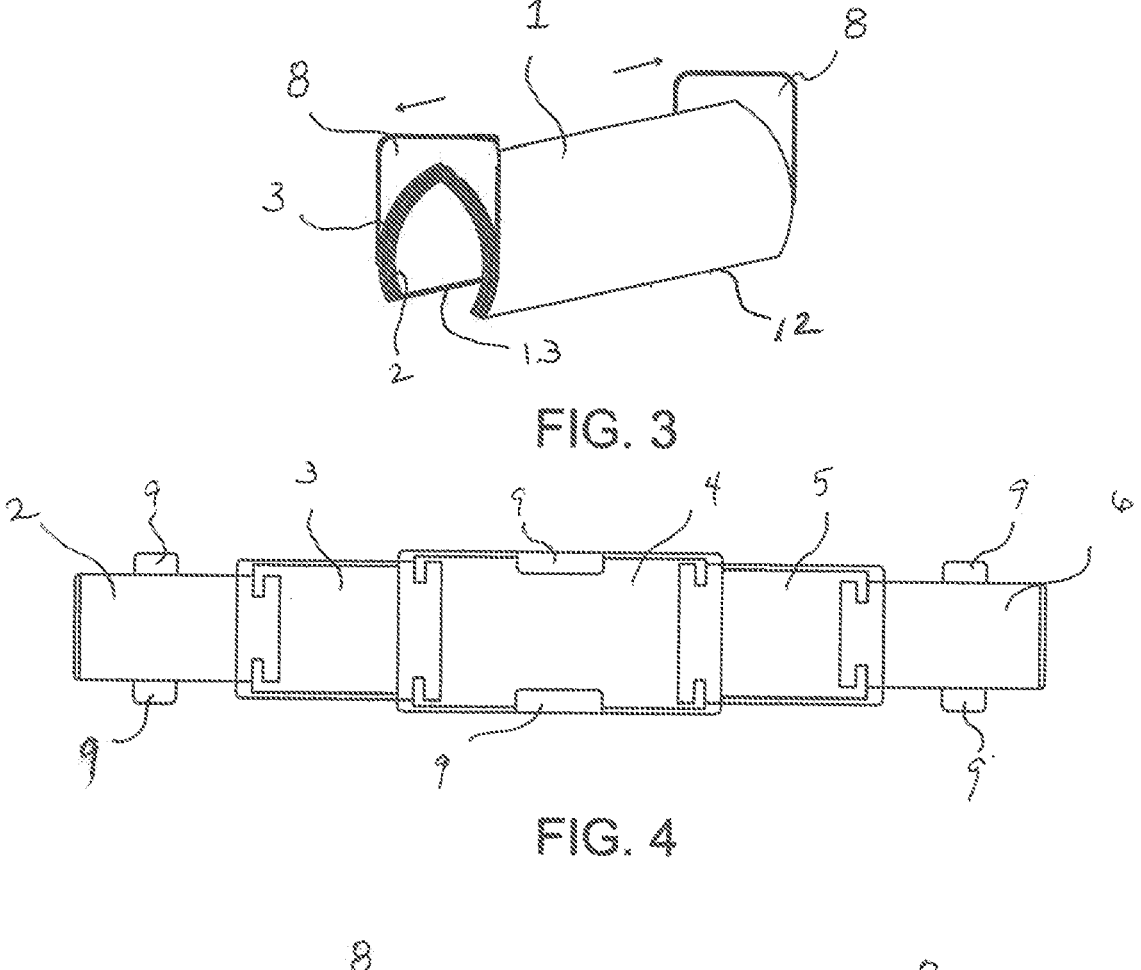
FIG. 3
FIG. 4
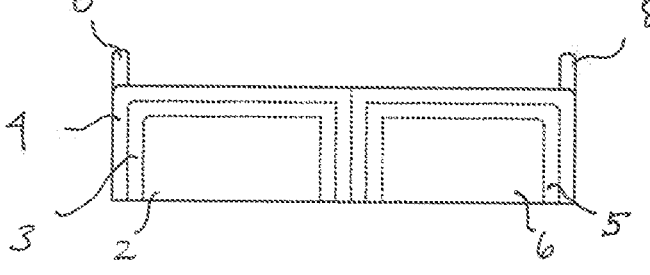
FIG. 5

METHOD/ PROCESS FLOW CHART

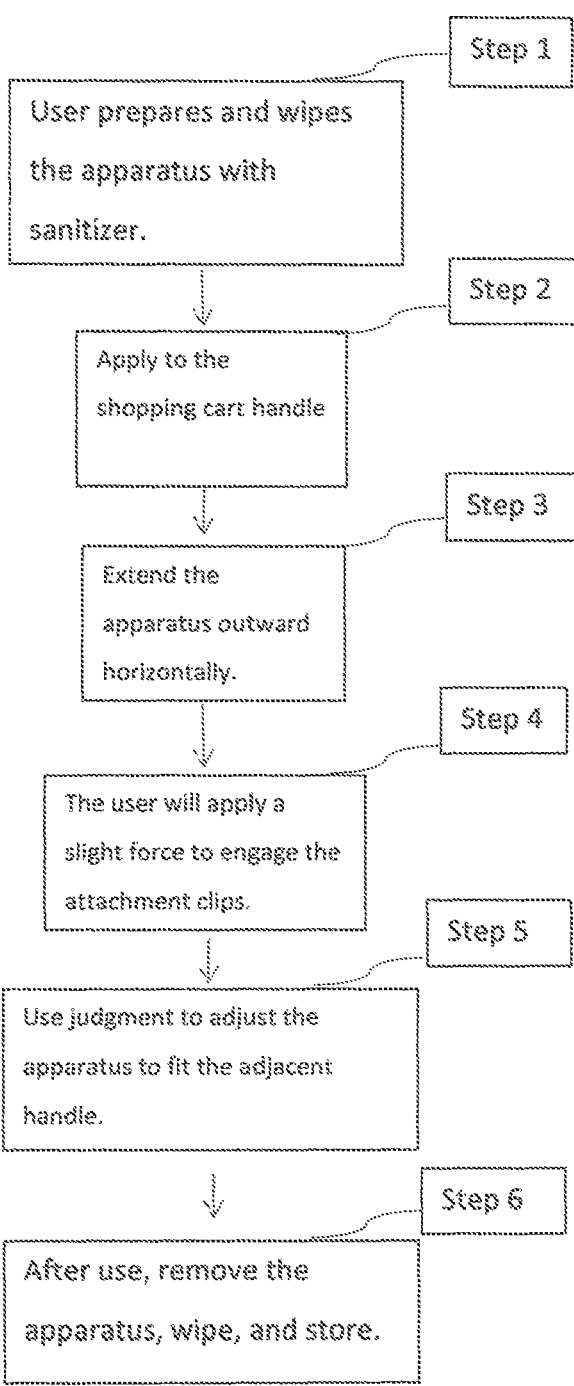

Step 1

User prepares and wipes the apparatus with sanitizer.

Step 2

Apply to the shopping cart handle

Step 3

Extend the apparatus outward horizontally.

Step 4

The user will apply a slight force to engage the attachment clips.

Step 5

Use judgment to adjust the apparatus to fit the adjacent handle.

Step 6

After use, remove the apparatus, wipe, and store.

Figure 14

VIRAL DISINFECTANT APPARATUS

CROSS-REFERENCE TO RELATED APPLICATIONS

None.

BACKGROUND OF THE INVENTION

Field of the Art

The disclosure relates to a low-cost durable antimicrobial shopping cart cover apparatus to prevent the transmission of harmful pathogens, including the COVID19 virus from one user to another when they use grocery shopping carts or similar devices comprising the apparatus herein described. The antimicrobial apparatus is a copper and silver oxide infused cover that may be easily installed and removed from existing shopping cart handles, providing for a convenient method of protecting users from contaminated surfaces. The embodiment allows a user to effectively keep users safe by allowing them to apply an adjustable protective apparatus on carts where a large number of people may touch such surfaces.

Discussion of the State of the Art

Commercial facilities include places such as grocery stores and malls that allow the general public to shop but are considered a heightened risk for health concerns due to exposure to surface pathogens. These facilities often include thousands of individuals who may be carrying viruses and other germs that can quickly spread to others. Most large metropolitan areas in the U.S. include a significant amount of the public shopping at grocery stores. Historically, these stores are becoming more communal with people socializing in large grocery chains. Utilizing public spaces and grocery carts in such locations can pose a threat to the public since complex and deadly viruses are a reality among our society. Accordingly, what is needed in the art is a novel invention that will allow users to protect themselves against surface viruses and germs while in public venues to ensure the safety and health of the public. What is further needed in the art is a novel manner of disinfecting an apparatus that can be removably affixed to a shopping cart handle to create a safer environment for the general public. The proposed embodiment is further ideal because its ultimate purpose is to allow users to utilize objects such as shopping carts in a safe manner that will be a welcome change for patrons.

SUMMARY OF THE INVENTION

Accordingly, the inventor has conceived, in a preferred embodiment of the invention, a viral disinfectant apparatus for public use.

According to a preferred embodiment of the invention, is a viral disinfectant apparatus that allows the user to protect themselves from harmful viruses in a novel manner. What is further disclosed is an apparatus that provides a way for the user to easily install a protective apparatus to a shopping cart while moving throughout a commercial space. What is further disclosed is an apparatus that can be adjustably fitted to a shopping cart and removed by a user for sanitizing purposes. The secure application and adjustability of the apparatus is a key component of the invention in that it provides the user the ability to apply the apparatus in a secure manner without concern for contracting viruses through surface contact by covering more surface space.

The objects and advantages of the present invention will become apparent to those skilled in the art when the following description of examples of structure representing the best modes contemplated at the present for practicing the invention is read in conjunction with the accompanying drawings wherein like references numerals refer to like or equivalent parts.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary and are not to be considered as limiting of the scope of the invention or the claims herein in any way.

FIG. 3 is a view of the viral disinfectant apparatus in a retracted position.

FIG. 4 is a bottom view of the viral disinfectant apparatus.

FIG. 5 is a view of the viral disinfectant apparatus to further show how the tubular segments are coupled together when in a retracted position.

FIG. 14 is a flow chart that outlines the process for using the viral disinfectant apparatus.

DETAILED DESCRIPTION

Figure 1:
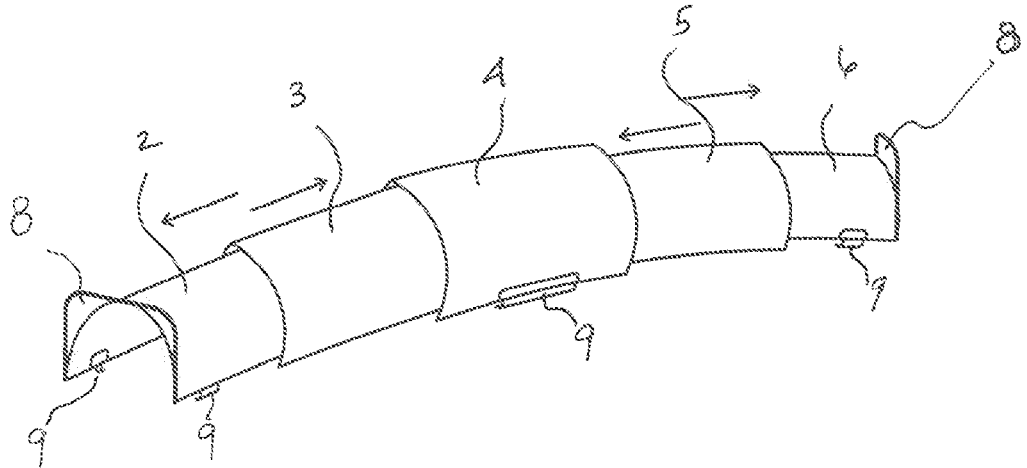
FIG. 1 is a perspective view of the viral disinfectant apparatus.

The present disclosure is best understood with reference to the detailed drawings and description set forth herein. Various embodiments have been discussed with reference to the drawings. However, the person skilled in the art will readily appreciate that the detailed descriptions provided herein with respect to the drawings are merely for explanatory purposes, as the apparatus, systems, and methods may extend beyond the described embodiments. For instance, the teachings presented and the needs of a particular application may yield multiple alternate and suitable approaches to implement the functionality of any detail described herein. Therefore, any approach may extend beyond certain implementation choices in the following embodiments.

The terms "a" or "an", as used herein, are defined as one, or more than one. The term "plurality", as used herein as defined as two, or more than two. The term "another", as used herein, is defined as at least a second or more. The terms "including" and/or "having", as used herein, are defined as comprising (i.e., open language), The term "coupled", as used herein, is defined as connected, although not necessarily directly, and not necessarily mechanically.

Reference throughout this document to "one embodiment", "certain embodiments", "an exemplary embodiment" or similar terms means that a particular feature, structure, or characteristic described in connection with the embodiment is included in at least one embodiment of the present invention, Thus, the appearances of such phrases or in various places throughout this specification are not necessarily all referring to the same embodiment. Furthermore, the particular features, structures or characteristics may be combined in any suitable manner in one or more embodiments without limitation.

Thus, the appearances of such phrases or in various pieces throughout this specification are not necessarily all referring to the same embodiment.

Numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present, in all embodiments.

Headings of sections provided in this patent application and the title of this patent application are for convenience only and are not to be taken as limiting the disclosure in any way.

Definitions

Reference throughout this document to "housing" or similar terms refers to the parts of the embodiment that make up the center portion of the apparatus and is in contact with the surface of the handle. Thus, the appearances of such phrases or in various places throughout this specification are not necessarily all referring to the same embodiment.

Reference throughout this document to "tubular segments", or similar terms refers to a various-sections that make up the housing of the apparatus. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to "adjustment grips", "grips", or similar terms refers to grips that are located at opposite ends of the housing to assist the user with adjusting the apparatus. It will be appreciated that the apparatus can be adjusted along the handle to ensure that the user covers as much of the surface as possible. Thus, the appearances of such phrases or in various places throughout this specification are not necessarily all referring to the same embodiment.

Reference throughout this document to "attachment clips", "clips", or similar terms refers to interconnecting clips utilized to securely hold the apparatus around the circumference of the handle bar to allow for maximum coverage along the bottom edge of the adjacent surface of the handle. Thus, the appearances of such phrases or in various places throughout this specification are not necessarily all referring to the same embodiment.

The present invention provides a viral disinfectant apparatus for use with a shopping cart or similar equipment to use while shopping in a method to prevent contamination from surface viruses and germs. In an embodiment, the apparatus includes an adjustable housing 1 that can be coupled to an adjoining shopping cart handle but is not limited to shopping carts but rather any object that may have a handle or rail for gripping. The embodiment can be utilized with various objects and equipment where the embodiment can adjust to the geometry of the adjoining object. As a non-limiting example, viral disinfectant apparatus can be used on bicycle handle bars or other commonly used objects that require a person to hold while operating. In an embodiment, viral disinfectant apparatus refers to an adjustable covering that can be extended and retracted to cover more surface. The viral disinfectant apparatus is useful for individuals who need to shop or transport items by using carts that may hold surface viruses. FIGS. 1-13 illustrate perspective views of a viral disinfectant apparatus for use with objects such as a shopping cart handle 7, in accordance with an embodiment. FIG. 1 illustrates how the apparatus is removably attached to the shopping cart handle 7. The housing 1 incorporates therein various attachment clips 9 for securing the apparatus to the handle 7, a plurality of tubular segments 2, 3, 4, 5, 6 comprising individual segments of varying sizes coupled together to allow for expansion and retraction by slidably pulling the two opposite adjustment grips 8 of the apparatus. In the preferred embodiment, a first tubular segment 2, a second tubular segment 3, a third tubular segment 4, a fourth tubular segment 5, and a fifth tubular segment 6 slidably connected together. The tubular members 2, 3, 4, 5, 6 is formed as a flexible plastic tube infused with copper and silver oxide particles thereof. Although plastic is the preferred material, other resilient materials could be used. In an embodiment, the viral disinfectant apparatus can be cleaned by utilizing sanitizer prior to use and once removed from the cart, the user can wipe the apparatus for reuse. The illustration further depicts the attachment clips 9 along the bottom edges of the apparatus.

Figure 2:
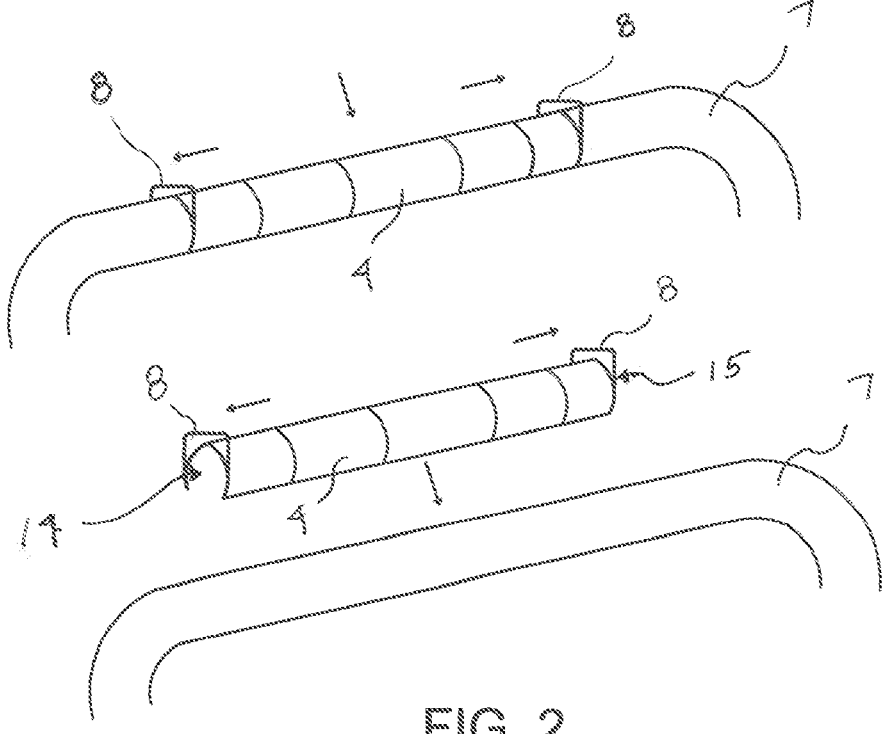
FIG. 2 is a perspective view of the viral disinfectant apparatus being coupled to a shopping cart handle.
Figure 6:
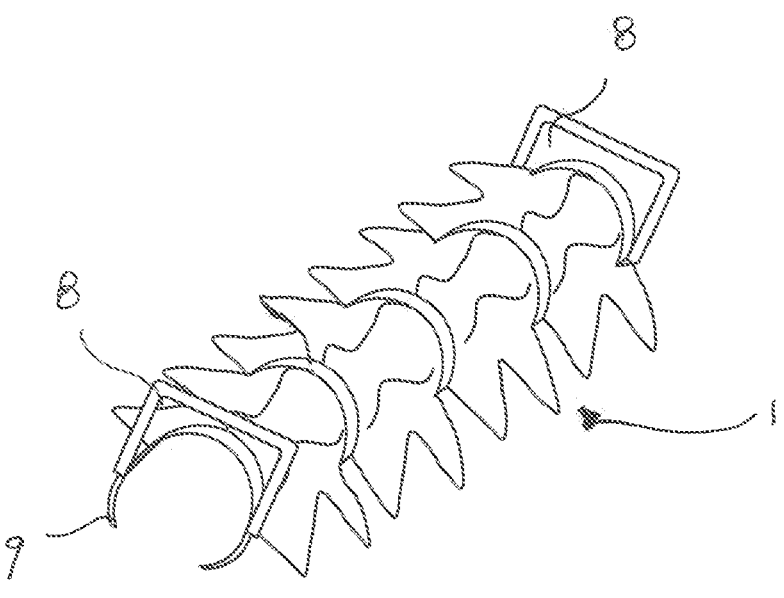
FIG. 6 is a perspective view of a disposable version of the viral disinfectant apparatus including the attachment clips.
Figure 7:
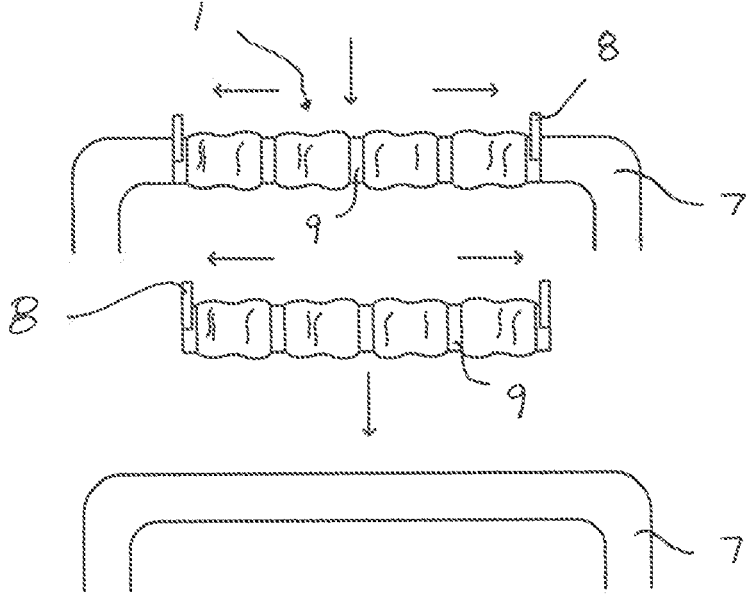
FIG. 7 is a perspective view of a disposable version of the viral disinfectant apparatus being coupled to a shopping cart handle.
Figure 8:
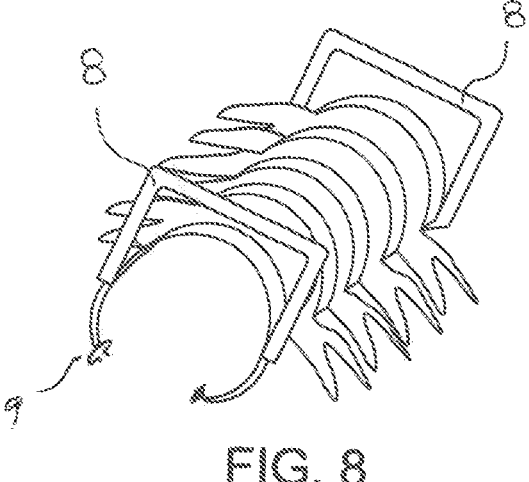
FIG. 8 is a perspective view of a disposable version of the viral disinfectant, apparatus while in a retracted position.
Figure 9:
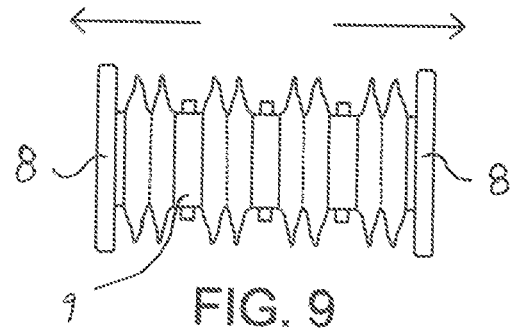
FIG. 9 is a side-view of a disposable version of the viral disinfectant apparatus while in a retracted position.
Figure 10:
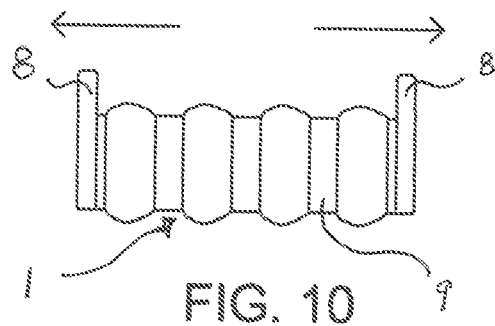
FIG. 10 is a side-view of a disposable version of the viral disinfectant apparatus while in an extended position to illustrate how the material extends along the horizontal direction.
Figure 13:
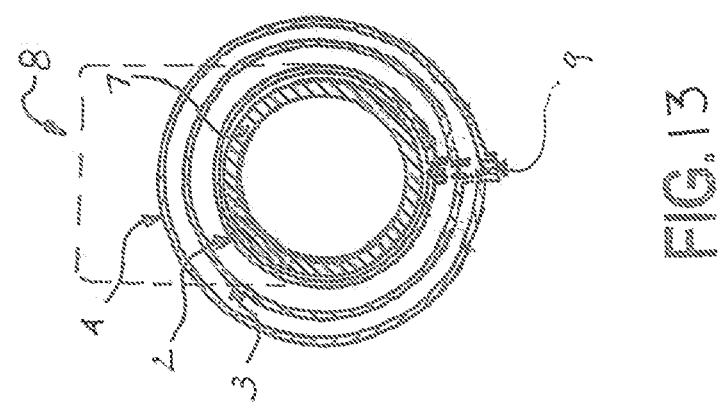
FIG. 13 is a cross-sectional view of the viral disinfectant apparatus installed on a handle to illustrate how the apparatus may cover additional surface area upon engaging the attachment clips.
Figure 12:
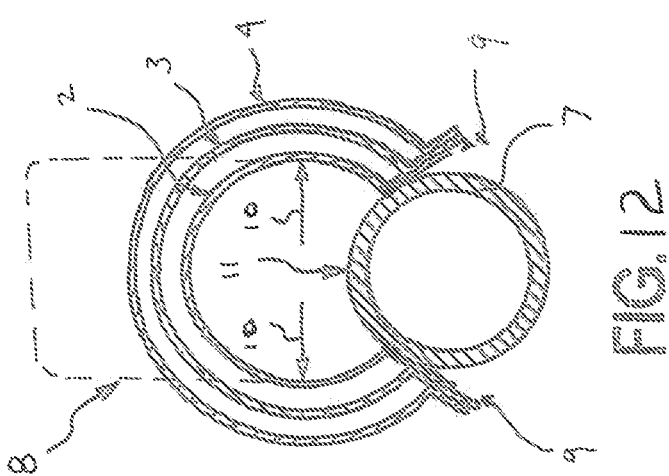
FIG. 12 is a cross-sectional view of the viral disinfectant apparatus being installed on a handle to illustrate how the apparatus can be applied along the top surface of the handle.
Figure 11:
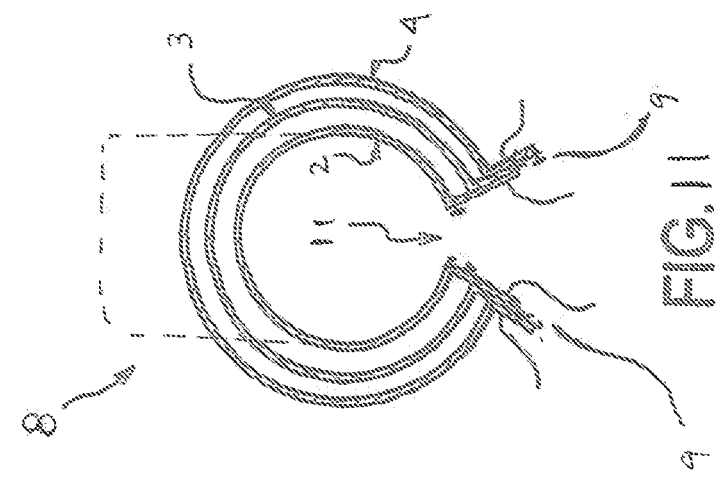
FIG. 11 is a cross-sectional view of the viral disinfectant apparatus prior to being installed on a handle.

In an embodiment, FIG. 2 is a schematic view of the viral disinfectant apparatus as r is being coupled to a shopping cart handle 7. The schematic further illustrates how the apparatus can be extended horizontally along the shopping cart handle 7 utilizing the adjustment grips 8 located along the first and second ends 14, 15 in a method to optimize the amount of surface area if necessary. Additionally, traditional coverings allow for exposed areas due to inadequate size comparison between the covering and the adjacent handle, it will be appreciated that the invention can be securely fastened to the circumference of the handle 7 surface by utilizing the attachment clips 9 to adjoin the opposite edges 12, 13 of the apparatus thus maximizing the amount surface covering and minimizing movement. The attachment clips 9 is ideal because when a user is potentially exposed to harmful surface viruses then it is beneficial to have an option to use a method of ensuring that the apparatus can extend to cover additional exposed surfaces while in use. FIG. 3 illustrates the adjustment grips 8, housing 1, first and second edges 12, 13 and the viral disinfectant apparatus in a retracted position for storage when not in use. 4 illustrates a bottom view of the apparatus and how the tubular segments 2, 3, 4, 5, 6 are slidingly connected when in an extended position. Additionally, the attachment clips 9 are shown along the bottom of the apparatus. FIG. 5 illustrates the position of the adjustment grips 8 and how the tubular segments 2, 3, 4, 5, 6 are coupled when placed in a retracted position by the user. In an alternate non-limiting embodiment, the viral disinfectant apparatus can be manufactured in a disposable version FIG. 6 to be discarded after use. Additionally, the embodiment may be designed in a various widths and lengths to satisfy a user's preference. For instance, where a user utilizes a commercial shopping cart handle 7 that is designed with a length much longer than an average handle for instance, in this case then the apparatus can be designed to accommodate varying sizes by adjusting to cover more surface length. FIG. 6 further depicts the engagement and receiving ends of the attachment clips 9 as well as the adjustment grips 8. The engagement and receiving ends of the attachment clips 9 allows the clips to connect in the secure position to fully hold the apparatus to the handle 7. In an embodiment, FIG. 7 is a schematic view of a disposable version of the viral disinfectant apparatus as it is being coupled to a shopping cart handle 7. The schematic further illustrates how the apparatus can be extended horizontally along the shopping cart handle 7 by utilizing the adjustment grips 8 in a method to optimize the amount surface area if necessary, Additionally, the schematic illustrates the attachment clips 9 located along the apparatus to securely attach the housing 1 to the handle 7. FIG. 8 is a perspective view of a disposable version of the viral disinfectant apparatus to illustrate the attachment clips 9, adjustment grips 8, and housing 1. FIG. 9 is a top-view of a disposable version of the viral disinfectant apparatus to illustrate the attachment clips 9, adjustment grips 8, and a representative illustration of how the housing is compressed while in a retracted position. FIG. 10 is a side-view of a disposable version of the viral disinfectant apparatus to illustrate the attachment clips 9, adjustment grips 8, and a representative illustration of how the housing 1 expands while in an extended position. FIG. 11 shows the viral disinfectant apparatus in cross section prior to engaging the attachment clips while installed on a shopping cart handle 7. The viral disinfectant apparatus is shown in cross-sectional view. In the cross-sectional view, FIG. 12, the apparatus is shown installed on the handle 7 wherein the attachment clips 9 are engaged to cover exposed surfaces of the handle 7. FIG. 11 is a cross-sectional view of the viral disinfectant apparatus prior to being installed on the shopping cart handle 7. The illustration shows a fainted view of the adjustment grip 8 along the first end of the apparatus. Additionally, the illustration shows a first tubular segment 2, second tubular segment 3, and third tubular segment 4 as a cross-section. The attachment clips 9 are shown coupled to the first tubular segment 2, and the third tubular segment 4. FIG. 12 is a cross-sectional view of the viral disinfectant apparatus being installed on a handle 7 expanded in a radial direction indicated by arrows 10 to expand slot 11 in order to receive the handle 7 in the interior of the tubular segments 2, 3, 4, 5, 6. The illustration shows a fainted view of the adjustment grip 8 along the first end of the apparatus. Additionally, the illustration shows a first tubular segment 2, second tubular segment 3, and third tubular segment 4 as a cross-section. The attachment clips 9 are shown coupled to the first tubular segment 2, and the third tubular segment 4. The illustration further shows how the apparatus can be applied along the top surface of the adjacent handle 7. FIG. 13 is a cross sectional view of the viral disinfectant apparatus installed on a handle 7 to illustrate how the apparatus may cover the full surface of the handle 7 by engaging the attachment clips 9. The illustration shows a first tubular segment 2, second tubular segment 3, third tubular segment 4, and a fainted view of the adjustment grip 8 along the first end of the apparatus. FIG. 14 is a process flow chart that outlines the process that a user may follow when using the viral disinfectant apparatus. At step 1 the user may decide to utilize the apparatus by removing from a stored area such as a personal carrying pouch wiping with an ordinary sanitizer. Then at step 2 the user can extend the apparatus outward in a horizontal fashion. Next at step 3, the user can apply a slight force to apply the apparatus to the shopping cart handle 7. At step 4, the user can use their judgment to adjust the apparatus along the handle 7 either extending the apparatus outward or inward depending on the length of the exposed handle. This will allow for optimal coverage of the handle 7 surface. It must be noted that the user may choose to use two or more apparatus to ensure that all surface areas of the handle 7 are covered. Step 5, explains how the apparatus can be removed, retracted, and sanitized for storage.

In an exemplary embodiment, the apparatus can be easily applied to an adjoining handle 7 by applying the apparatus to the top edge of the handle. The flexible design and geometry of the apparatus will allow the material to expand and snap securely to the handle. Once the apparatus is securely in place along the handle the tubular segments can be extended to allow exposed surfaces to be covered, and the user can utilize the attachment clips 9 which includes an engagement and receiving clasp along the first and second edges 12, 13 of the apparatus thus allowing for optimal protection. To further elaborate, once the attachment clips 9 engage with the receiving portion along the first and second edges 12, 13, the apparatus will be securely fastened to close the slot 11 as the user engage the clips 9. This engagement by the attachment clips 9 causes the first and second edges 12, 13 of the apparatus to cover more exposed portions of the handle 7 surface while in a fastened position. It will be appreciated that when the apparatus is removed from the handle, the user may place the apparatus in a retracted position for storage by merely applying a slight force to the first and second ends 14, 15 of the apparatus. The key to the embodiment is that the housing 1 is infused with antimicrobial material for killing viruses, the apparatus is adjustable for maximum coverage, and a user has the option of sanitizing the apparatus for reuse or discarding as an optional disposable version.

EXEMPLARY EMBODIMENTS

FIG. 1 is a perspective view of a viral disinfectant apparatus, according to a preferred embodiment of the invention.

FIG. 2 is a perspective view of the viral disinfectant apparatus being coupled to a shopping cart handle, according to a preferred embodiment of the invention.

FIG. 3 is a view of the viral disinfectant apparatus in a retracted position according to a preferred embodiment of the invention.

FIG. 4 is a bottom view of the viral disinfectant apparatus, according to a preferred embodiment of the invention.

FIG. 5 is a view of the viral disinfectant apparatus to further show how the tubular segments are coupled together when in a retracted position according to a preferred embodiment of the invention.

FIG. 6 is a perspective view of a disposable version of the viral disinfectant apparatus in the attachment clips, according to a preferred embodiment of the invention.

FIG. 7 is a perspective view of a disposable version of the viral disinfectant apparatus being coupled to a shopping cart handle according to a preferred embodiment of the invention.

FIG. 8 is a perspective of a disposable version of the viral disinfectant apparatus while in a retracted position, according to a preferred embodiment of the invention.

FIG. 9 is a side-view of a disposable version of the viral disinfectant apparatus while in a retracted position, according to a preferred embodiment of the invention.

FIG. 10 is a side-view of a disposable version of the viral disinfectant apparatus while in an extended position to illustrate how the material extends along the horizontal direction, according to a preferred embodiment of the invention.

FIG. 11 is a cross-sectional view of the viral disinfectant apparatus prior to being installed on a handle, according to a preferred embodiment of the invention.

FIG. 12 is a cross-sectional view of the viral disinfectant apparatus being installed on a handle to illustrate how the apparatus can be applied along to top surface of the handle, according to a preferred embodiment of the invention.

FIG. 13 is a cross-sectional view of the viral disinfectant apparatus installed on a handle to illustrate how the apparatus may cover additional surface area upon engaging the attachment clips, according to a preferred embodiment of the invention.

FIG. 14 is a flow chart that outlines the process for using the viral disinfectant apparatus, according to a preferred embodiment of the invention.

The skilled person will be aware of a range of possible modifications of the various embodiments described above. Accordingly, the present invention is defined by the claims and their equivalents.

What is claimed is:

1. A method of applying a microbial disinfectant apparatus for protecting against contamination, comprising: providing a microbial disinfectant apparatus for use with shopping cart handles, wherein the apparatus comprises an adjustable housing; a user removably attaching the apparatus with the shopping cart handle, wherein the housing is wiped clean with sanitizer prior to and upon attaching to shopping cart handle, wherein the housing couples to the shopping cart handle by flexible material upon application of the apparatus, adjustably securing the apparatus to the shopping cart handle; and wherein the apparatus is adjusted along the shopping cart handle in a horizontal position depending on orientation of the shopping cart handle; wherein the user will apply force to engage the attachment clips; wherein after use the user will remove the apparatus, wipe, and store.

2. The method as claimed in claim 1, wherein the housing comprising: at least two tubular segments; at least two attachment clips; and at least two adjustment grips.

* * * * *